United States Patent
Andree et al.

(10) Patent No.: US 6,251,828 B1
(45) Date of Patent: *Jun. 26, 2001

(54) SUBSTITUTED PHENYLURACILS

(75) Inventors: Roland Andree; Mark Wilhelm Drewes, both of Langenfeld; Markus Dollinger; Hans-Joachim Santel, both of Leverkusen, all of (DE)

(73) Assignee: Bayer Aktiengesellschaft, Leverkusen (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/983,631

(22) PCT Filed: Jul. 22, 1996

(86) PCT No.: PCT/EP96/03223

§ 371 Date: Jan. 23, 1998

§ 102(e) Date: Jan. 23, 1998

(87) PCT Pub. No.: WO97/05118

PCT Pub. Date: Feb. 13, 1997

(30) Foreign Application Priority Data

Aug. 1, 1995 (DE) ................................ 195 28 186

(51) Int. Cl.$^7$ .................... C07D 239/54; A01N 43/54
(52) U.S. Cl. ................... 504/243; 544/296; 544/310; 544/311; 544/312; 544/309; 544/314
(58) Field of Search ................. 504/243; 544/310, 544/312, 314, 309, 311, 296

(56) References Cited

U.S. PATENT DOCUMENTS 4,812,164 * 3/1989 Wenger et al. ............... 544/313
4,859,229 * 8/1989 Wenger et al. ............... 544/313
4,979,982 12/1990 Brouwer et al. ............... 544/314
5,981,436 * 11/1999 Drewes et al. ............... 544/310
6,057,269 * 5/2000 Klintz et al. ............... 544/310

FOREIGN PATENT DOCUMENTS 0 255 047   2/1988 (EP).
WO 93/06090  4/1993 (WO).

* cited by examiner

Primary Examiner—John M. Ford
(74) Attorney, Agent, or Firm—Norris McLaughlin & Marcus

(57) ABSTRACT

The invention relates to novel substituted phenyluracils of the general formula (I)

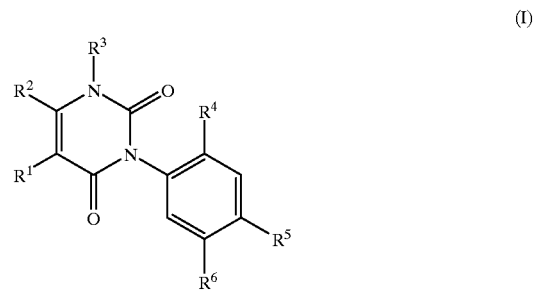

(I)

in which $R^1$, $R^2$, $R^3$, $R^4$, $R^5$ and $R^6$ are each as defined in the description, to processes for their preparation, to novel intermediates and to their use as herbicides.

6 Claims, No Drawings

SUBSTITUTED PHENYLURACILS

The invention relates to novel substituted phenyluracils, to processes for their preparation, to novel intermediates and to their use as herbicides.

It is known that certain substituted uracils have herbicidal properties (cf. EP 408382/U.S. Pat. No. 5,084,084/U.S. Pat. No. 5,127,935/U.S. Pat. No. 5,154,755, EP 563384, EP 648749, WO 91/00278, U.S. Pat. No. 4,979,982, U.S. Pat. No. 5,169,430, DE 4329537). However, these compounds have hitherto not attained any major importance.

This invention, accordingly, provides the novel substituted phenyluracils of the general formula (I)

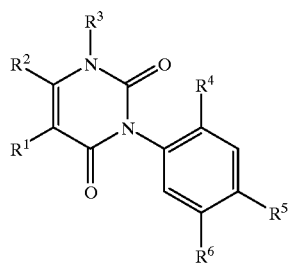

(I)

in which

R$^1$ represents hydrogen, halogen or optionally substituted alkyl,

R$^2$ represents optionally substituted alkyl,

R$^3$ represents hydrogen, amino or respectively optionally substituted alkyl, alkenyl or alkinyl, R$^4$ represents hydrogen, cyano or halogen, R$^5$ represents cyano or thiocarbamoyl, and R$^6$ represents one of the groupings below

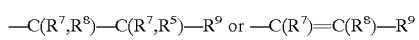

—C(R$^7$,R$^8$)—C(R$^7$,R$^5$)—R$^9$ or —C(R$^7$)=C(R$^8$)—R$^9$ in which

R$^7$ and R$^8$ are identical or different and each represents independently of the other hydrogen, hydroxyl, mercapto, halogen or respectively optionally substituted alkyl, alkoxy or alkylthio, and R$^9$ represents cyano, formyl, alkylcarbonyl, the grouping —CO—OR$^{10}$ or the grouping —CO—N(R$^{11}$,R$^{12}$), where R$^{10}$ represents hydrogen or represents a respectively optionally substituted radical from the group consisting of alkyl, alkenyl, alkinyl, cycloalkyl, cycloalkylalkyl, aryl, arylalkyl, heterocyclyl and heterocyclylalkyl, R$^{11}$ represents hydrogen or represents a respectively optionally substituted radical from the group consisting of alkyl, alkoxy, alkenyl and alkinyl, and R$^{12}$ represents hydrogen or represents a respectively optionally substituted radical from the group consisting of alkyl, alkenyl, alkinyl, cycloalkyl, cycloalkylalkyl, aryl, arylalkyl, heterocyclyl and heterocyclylalkyl, or together with R$^{11}$ represents alkanediyl.

The novel substituted phenyluracils of the general formula (I) are obtained when (a) aminophenyluracils of the general formula (II)

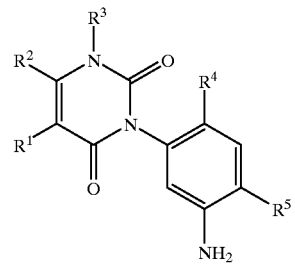

(II)

in which

R$^1$, R$^2$, R$^3$, R$^4$ and R$^5$ are each as defined above, or acid adducts of compounds of the formula (II)

are reacted with an alkali metal nitrite or alkyl nitrite and with a hydrogen halide (HX$^1$) or a metal halide (MX$^1$), if appropriate in the presence of a diluent, and the resulting diazonium salts of the general formula (III)

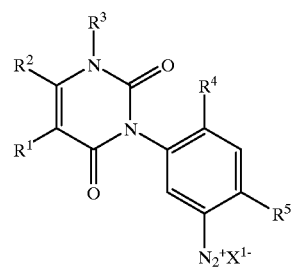

(III)

in which

R$^1$, R$^2$, R$^3$, R$^4$ and R$^5$ are each as defined above and

X$^1$ represents halogen, are reacted with acrylic acid derivatives of the general formula (IV)

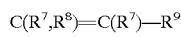

C(R$^7$,R$^8$)=C(R$^7$)—R$^9$ (IV)

in which

R$^7$, R$^8$ and R$^9$ are each as defined above, in the presence of hydrogen halides (HX$^1$), if appropriate in the presence of catalysts, if appropriate in the presence of water and if appropriate in the presence of the organic solvent employed initially, or (b) substituted phenyluracils of the general formula (Ia)

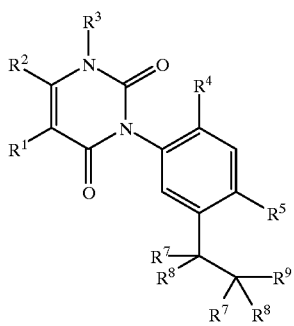

(Ia)

in which
R¹, R², R³, R⁴, R⁵, R⁷, R⁸ and R⁹ are each as defined above,
but where at least one of the radicals R⁷/R⁸ represents hydrogen and at least one further radical R⁷/R⁸ in a position vicinal to the first represents halogen
are reacted with an acid acceptor, if appropriate in the presence of a diluent.

It is also possible to convert the compounds of the general formula (I) into other compounds of the general formula (I) according to the above definition using other conventional methods, for example by amination or alkylation (e.g. R³: H→NH₂, H→CH₃), reaction with hydrogen sulphide (e.g. R⁵: CN→CSNH₂), nucleophilic substitution (e.g. R⁸: Cl→SCH₃), if appropriate addition of hydrogen, halogen or hydrogen halide to a C—C double bond (cf. definition of R⁶), hydrolysis (e.g. R⁹: CN→COOH).

If the compounds of the formula (I) according to the invention contain olefinic double bonds (cf. definition of R⁶), the invention relates both to the individual E and Z or cis and trans isomers separable by conventional methods, and also to any mixtures of these isomers.

The novel substituted phenyluracils of the general formula (I) have strong herbicidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably fluorine, chlorine or bromine, in particular fluorine or chlorine.

The invention preferably provides compounds of the formula (I) in which
R¹ represents hydrogen, fluorine, chlorine, bromine or optionally fluorine- and/or chlorine-substituted $C_1$–$C_4$-alkyl,
R² represents optionally fluorine- and/or chlorine-substituted $C_1$–$C_4$-alkyl,
R³ represents hydrogen, amino, represents optionally cyano-, fluorine-, chlorine- or $C_1$–$C_4$-alkoxy-substituted $C_1$–$C_6$-alkyl or represents optionally fluorine- and/or chlorine-substituted $C_2$–$C_6$-alkenyl or $C_2$–$C_6$-alkinyl,
R⁴ represents hydrogen, cyano, fluorine or chlorine,
R⁵ represents cyano or thiocarbamoyl, and
R⁶ represents one of the groupings below

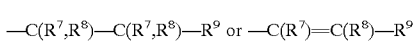

in which

R⁷ and R⁸ are identical or different and each represents independently of the other hydrogen, hydroxyl, mercapto, fluorine, chlorine, bromine or respectively optionally cyano-, fluorine-, chlorine- or $C_1$–$C_4$-alkoxy-substituted $C_1$–$C_4$-alkyl, $C_1$–$C_4$-alkoxy or $C_1$–$C_4$-alkylthio, and R⁹ represents cyano, formyl, $C_1$–$C_4$-alkyl-carbonyl, the grouping —CO—OR¹⁰ or the grouping —CO—N(R¹¹, R¹²), where R¹⁰ represents hydrogen or represents optionally cyano-, fluorine-, chlorine- or $C_1$–$C_4$-alkoxy-substituted $C_1$–$C_{10}$-alkyl, R¹⁰ furthermore represents respectively optionally fluorine-, chlorine- or bromine-substituted $C_3$–$C_{10}$-alkenyl or $C_3$–$C_{10}$-alkinyl, R¹⁰ furthermore represents respectively optionally cyano-, fluorine-, chlorine-, bromine-, $C_1$–$C_4$-alkyl- or $C_1$–$C_4$-alkoxy-carbonyl-substituted $C_3$–$C_6$-cycloalklyl or $C_3$–$C_6$-cycloalkyl-$C_1$–$C_4$-alkyl, R¹⁰ furthermore represents respectively optionally cyano-, fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio- or $C_1$–$C_4$-alkoxy-carbonyl-substituted phenyl, phenyl-$C_1$–$C_4$-alkyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxaazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl, R¹¹ represents hydrogen or represents respectively optionally cyano-, fluorine-, chlorine- or $C_1$–$C_4$-alkoxy-substituted $C_1$–$C_6$-alkyl or $C_1$–$C_6$-alkoxy, R¹¹ furthermore represents respectively optionally fluorine-, chlorine- or bromine-substituted $C_3$–$C_6$-alkenyl or $C_3$–$C_6$-alkinyl, and R¹² represents hydrogen or represents optionally cyano-, fluorine-, chlorine- or $C_1$–$C_4$-alkoxy-substituted $C_1$–$C_{10}$-alkyl, R¹² furthermore represents respectively optionally fluorine-, chlorine- or bromine-substituted $C_3$–$C_{10}$-alkenyl or $C_3$–$C_{10}$-alkinyl, R¹² furthermore represents respectively optionally cyano-, fluorine-, chlorine-, bromine-, $C_1$–$C_4$-alkyl- or $C_1$–$C_4$-alkoxy-carbonyl-substituted $C_3$–$C_6$-cycloalkyl or $C_3$–$C_6$-cycloalkyl-$C_1$–$C_4$-alkyl, R¹² furthermore represents respectively optionally cyano-, fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio- or $C_1$–$C_4$-alkoxy-carbonyl-substituted phenyl, phenyl-$C_1$–$C_4$-alkyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxadiazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl or together with $R^{11}$ represents $C_2$–$C_6$-alkanediyl.

The invention in particular provides compounds of the formula (I) in which $R^1$ represents hydrogen, fluorine, chlorine, bromine or optionally fluorine- and/or chlorine-substituted methyl or ethyl, $R^2$ represents optionally fluorine- and/or chlorine-substituted methyl or ethyl, $R^3$ represents hydrogen, amino, represents optionally cyano-, fluorine-, chlorine-, methoxy- or ethoxy-substituted methyl, ethyl, n- or i-propyl, n-, i-, s- or t-butyl, or represents optionally fluorine- and/or chlorine-substituted propenyl, butenyl, propinyl or butinyl, $R^4$ represents hydrogen, fluorine or chlorine, $R^5$ represents cyano or thiocarbamoyl, and $R^6$ represents one of the groupings below

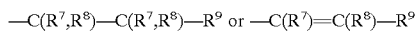

—C($R^7$,$R^8$)—C($R^7$,$R^8$)—$R^9$ or —C($R^7$)=C($R^8$)—$R^9$ in which $R^7$ and $R^8$ are identical or different and each represents independently of the other hydrogen, fluorine, chlorine, bromine or respectively optionally cyano-, fluorine-, chlorine-, methoxy- or ethoxy-substituted methyl, ethyl, methoxy, ethoxy, methylthio or ethylthio, and $R^9$ represents cyano, the grouping —CO—O$R^{10}$ or the grouping —CO—N($R^{11}$,$R^{12}$), where $R^{10}$ represents hydrogen or represents respectively optionally cyano-, fluorine-, chlorine-, methoxy- or ethoxy-substituted methyl, ethyl, n- or i-propyl, n-, i-, s- or t-butyl, n-, i-, s- or t-pentyl, $R^{10}$ furthermore represents respectively optionally fluorine-, chlorine- or bromine-substituted propenyl, butenyl, pentenyl, propinyl, butinyl or pentinyl, $R^{10}$ furthermore represents respectively optionally cyano-, fluorine-, chlorine-, bromine-, methyl-, ethyl-, methoxycarbonyl- or ethoxycarbonyl-substituted cyclopropyl, cyclobutyl, cyclopentyl, cyclohexyl, cyclopropylmethyl, cyclobutylmethyl, cyclopentylmethyl or cyclohexylmethyl, $R^{10}$ furthermore represents respectively optionally cyano-, fluorine-, chlorine-, bromine-, methyl-, ethyl-, trifluoromethyl-, methoxy-, ethoxy-, difluoromethoxy-, trifluoromethoxy-, methylthio-, ethylthio-, difluoromethylthio-, trifluoromethyl-, methoxycarbonyl- or ethoxycarbonyl-substituted phenyl, phenylmethyl, phenylethyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl, $R^{11}$ represents hydrogen or represents respectively optionally cyano-, fluorine-, chlorine-, methoxy- or ethoxy-substituted methyl, ethyl, methoxy or ethoxy, $R^{11}$ furthermore represents respectively optionally fluorine-, chlorine- or bromine-substituted propenyl or propinyl, and $R^{12}$ represents hydrogen or represents optionally cyano-, fluorine-, chlorine-, methoxy- or ethoxy-substituted methyl, ethyl, n- or i-propyl, n-, i-, s- or t-butyl, n-, i-, s- or t-pentyl, $R^{12}$ furthermore represents respectively optionally fluorine-, chlorine- or bromine-substituted propenyl, butenyl, pentenyl, propinyl, butinyl or pentinyl, represents respectively optionally cyano-, fluorine-, chlorine-, bromine-, methyl-, ethyl-, methoxycarbonyl- or ethoxycarbonyl-substituted cyclopropyl, cyclobutyl, cyclopentyl, cyclohexyl, cyclopropylmethyl, cyclobutylmethyl, cyclopentylmethyl or cyclohexylmethyl, $R^{12}$ furthermore represents respectively optionally cyano-, fluorine-, chlorine-, bromine-, methyl-, ethyl-, trifluoromethyl-, methoxy-, ethoxy-, difluoromethoxy-, trifluoromethoxy-, methylthio-, ethylthio-, difluoromethylthio-, trifluoromethylthio-, methoxycarbonyl- or ethoxycarbonyl-substituted phenyl, phenylmethyl, phenylethyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl.

The general or preferred radical definitions listed above are valid both for the end products of the formula (I) and, in a corresponding manner, also for the starting materials or intermediates which are required in each case for the preparation. These radical definitions can be combined with each other at will, i.e. combinations between the given preferred ranges are also possible.

Examples of the compounds of the formula (I) according to the invention are listed in the groups below.

Group 1

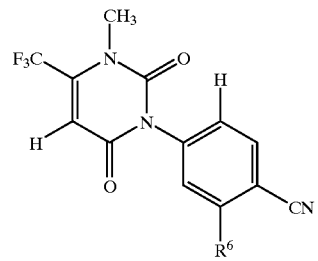

$R^6$ has in this case for example the meanings given in the list below:

2-cyano-ethenyl, 2-cyano-1-methyl-ethenyl, 2-cyano-1-chloro-ethenyl, 2-cyano-2-chloro-ethenyl, 2-cyano-1-bromo-ethenyl, 2-cyano-2-bromo-ethenyl, 2-cyano-propenyl, 2-cyano-ethyl, 2-cyano-2-fluoro-ethyl, 2-cyano-2-chloro-ethyl, 2-cyano-2-bromo-ethyl, 2-cyano-1,2-dichloro-ethyl, 2-cyano-1,2-dibromo-ethyl, 2-cyano-2,2-dichloro-ethyl, 2-cyano-2-chloro-1-methyl-ethyl, 2-cyano-2-chloro-1,2-dimethyl-ethyl, 2-cyano-2-chloro-propyl, 2-carboxy-ethenyl, 2-carboxy-1-methyl-ethenyl, 2-carboxy-1-chloro-ethenyl, 2-carboxy-2-chloro-ethenyl, 2-carboxy-1-bromo-ethenyl, 2-carboxy-2-bromo-ethenyl, 2-carboxy-propenyl, 2-carboxy-ethyl, 2-carboxy-2-fluoro-ethyl, 2-carboxy-2-chloro-ethyl, 2-carboxy-2-bromo-ethyl, 2-carboxy-1,2- dichloro-ethyl, 2-carboxy-1,2-dibromo-ethyl, 2-carboxy-2,2-dichloro-ethyl, 2-carboxy-2-chloro-1-methyl-ethyl, 2-carboxy-2-chloro-1,2-dimethyl-ethyl, 2-carboxy-2-chloro-propyl, 2-methoxycarbonyl-ethenyl, 2-methoxycarbonyl-1-methyl-ethenyl, 2-methoxycarbonyl-1-chloro-ethenyl, 2-methoxycarbonyl-2-chloro-ethenyl, 2-methoxycarbonyl-1-bromo-ethenyl, 2-methoxycarbonyl-2-bromo-ethenyl, 2-methoxycarbonyl-propenyl, 2-methoxycarbonyl-ethyl, 2-methoxycarbonyl-2-fluoro-ethyl, 2-methoxycarbonyl-2-chloro-ethyl, 2-methoxycarbonyl-2-bromo-ethyl, 2-methoxycarbonyl-1,2-dichloro-ethyl, 2-methoxycarbonyl-1,2-dibromo-ethyl, 2-methoxycarbonyl-2,2-dichloro-ethyl, 2-methoxycarbonyl-2-chloro-1-methyl-ethyl, 2-methoxycarbonyl-2-chloro-1,2-dimethyl-ethyl, 2-methoxycarbonyl-2-chloro-propyl, 2-ethoxycarbonyl-ethenyl, 2-ethoxycarbonyl-1-methyl-ethenyl, 2-ethoxycarbonyl-1-chloro-ethenyl, 2-ethoxycarbonyl-2-chloro-ethenyl, 2-ethoxycarbonyl-1-bromo-ethenyl, 2-ethoxycarbonyl-2-bromo-ethenyl, 2-ethoxycarbonyl-propenyl, 2-ethoxycarbonyl-ethyl, 2-ethoxycarbonyl-2-fluoro-ethyl, 2-ethoxycarbonyl-2-chloro-ethyl, 2-ethoxycarbonyl-2-bromo-ethyl, 2-ethoxycarbonyl-1,2-dichloro-ethyl, 2-ethoxycarbonyl-1,2-dibromo-ethyl, 2-ethoxycarbonyl-2,2-dichloro-ethyl, 2-ethoxycarbonyl-2chloro-1-methyl-ethyl, 2-ethoxycarbonyl-2-chloro-1,2-dimethyl-ethyl, 2-ethoxycarbonyl-2-chloro-propyl.

Group 2

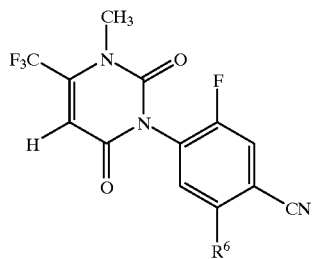

$R^6$ has in this case for example the meanings listed above in Group 1.

Group 3

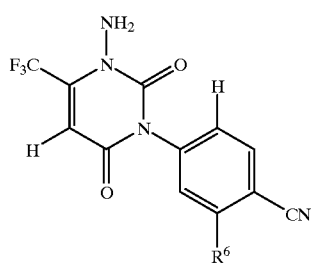

$R^6$ has in this case for example the meanings listed above in Group 1.

Group 4

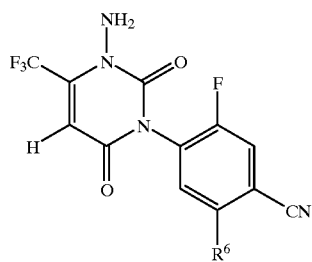

$R^6$ has in this case for example the meanings listed above in Group 1.

Group 5

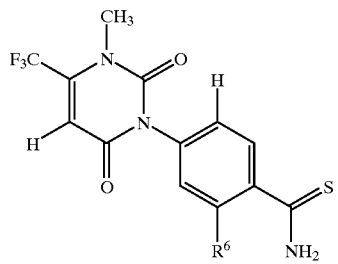

$R^6$ has in this case for example the meanings listed above in Group 1.

Group 6

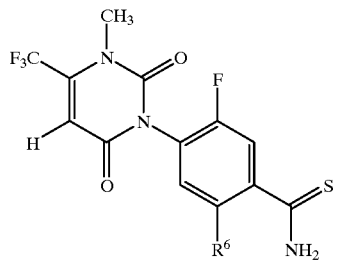

$R^6$ has in this case for example the meanings listed above in Group 1.

Group 7

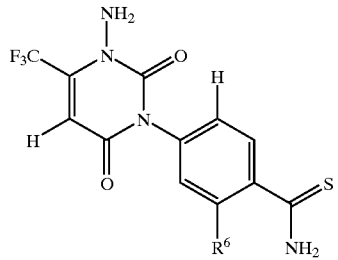

$R^6$ has in this case for example the meanings listed above in Group 1.

Group 8

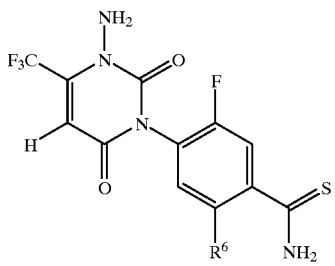

$R^6$ has in this case for example the meanings listed above in Group 1.

Group 9

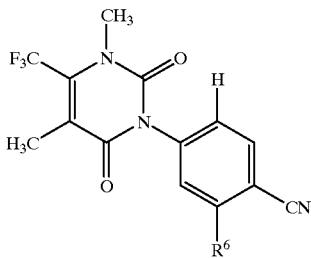

$R^6$ has in this case for example the meanings listed above in Group 1.

Group 10

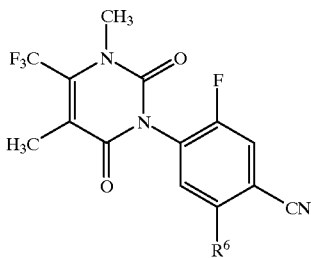

$R^6$ has in this case for example the meanings listed above in Group 1.

Group 11

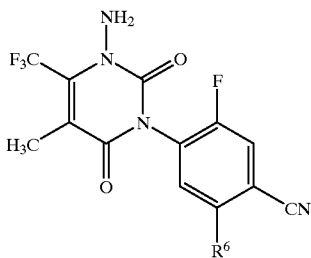

$R^6$ has in this case for example the meanings listed above in Group 1.

Group 12

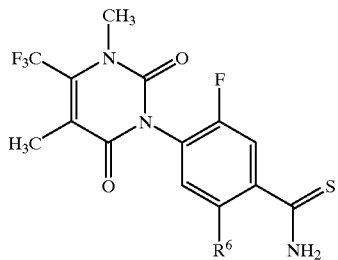

$R^6$ has in this case for example the meanings listed above in Group 1.

Group 13

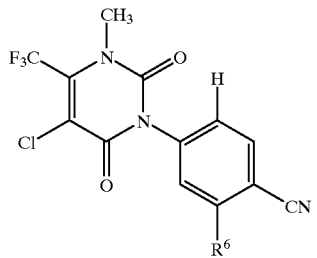

$R^6$ has in this case for example the meanings listed above in Group 1.

Group 14

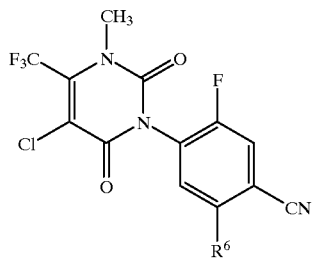

$R^6$ has in this case for example the meanings listed above in Group 1.

Group 15

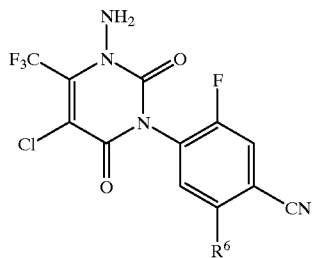

$R^6$ has in this case for example the meanings listed above in Group 1.

Group 16

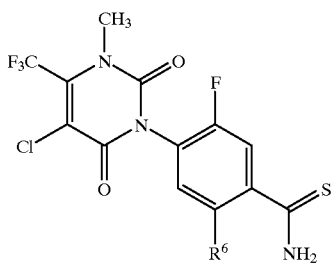

$R^6$ has in this case for example the meanings listed above in Group 1.

Group 17

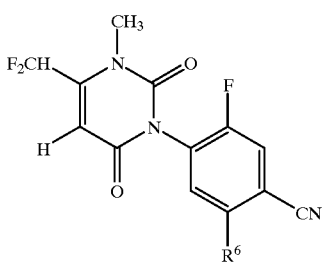

$R^6$ has in this case for example the meanings listed above in Group 1.

Group 18

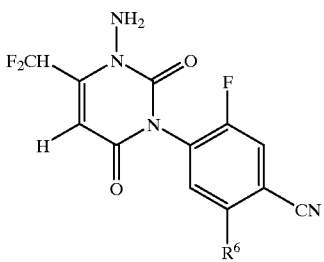

$R^6$ has in this case for example the meanings listed above in Group 1.

Group 19

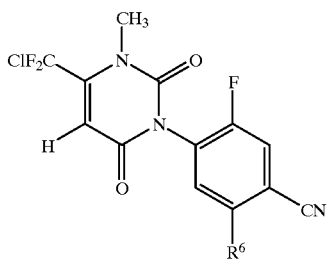

$R^6$ has in this case for example the meanings listed above in Group 1.

Group 20

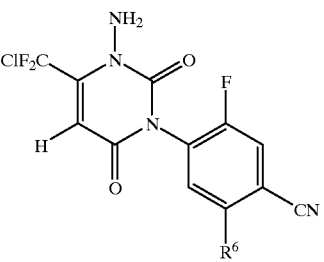

$R^6$ has in this case for example the meanings listed above in Group 1.

Group 21

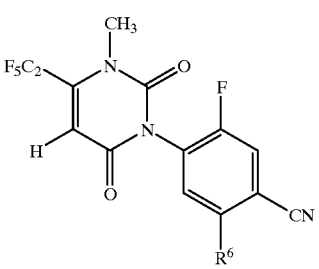

$R^6$ has in this case for example the meanings listed above in Group 1.

Group 22

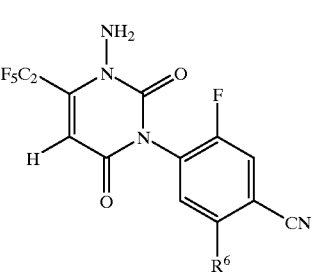

$R^6$ has in this case for example the meanings listed above in Group 1.

Using, for example, 1-(5-amino-4-cyano-2-fluorophenyl)-3,6-dihydro-2,6-dioxo-3-methyl-4-trifluoromethyl-1(2H)-pyrimidine, sodium nitrite and hydrochloric acid and then methyl acrylate as starting materials, the course of the reaction in the process (a) according to the invention can be illustrated by the following scheme:

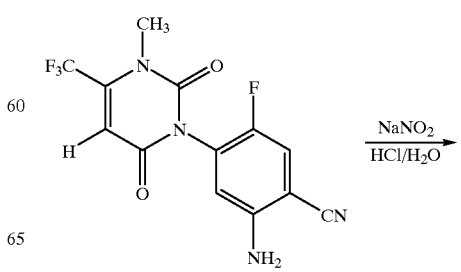

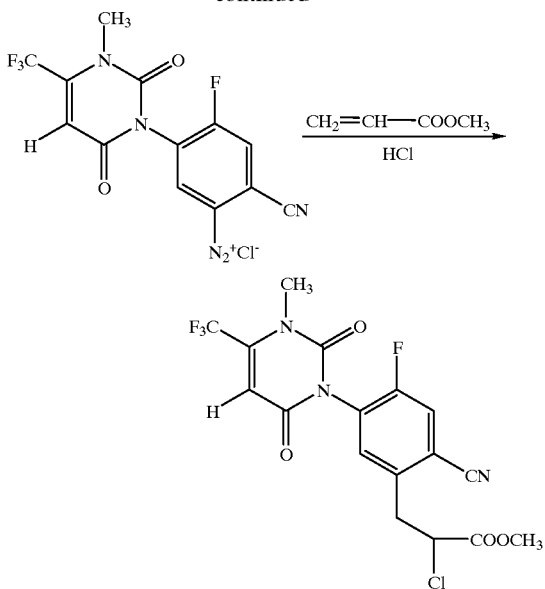

Using, for example, 1-[4-cyano-2-fluoro-5-(2-chloro-2-methoxycarbonyl-ethyl)-phenyl]-3,6-dihydro-2,6-dioxo-3,5-dimethyl-4-trifluoromethyl-1(2H)-pyrimidine as starting material and triethylamine as acid acceptor, the course of the reaction in the process (b) according to the invention can be illustrated by the following scheme:

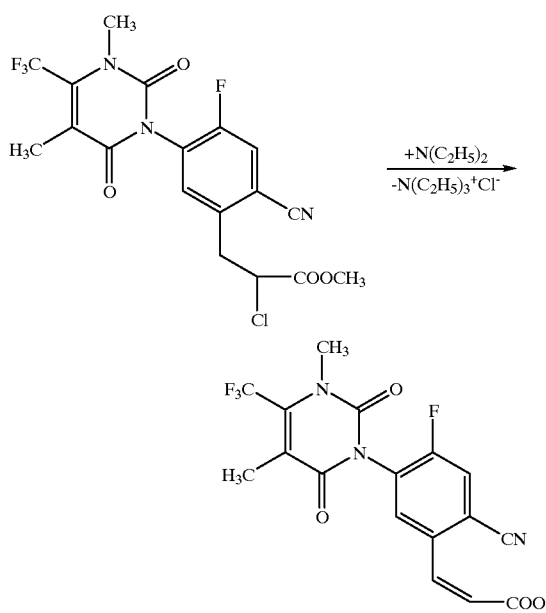

The formula (II) provides a general definition of the aminophenyluracils to be used as starting materials in the process (a) according to the invention for preparing the compounds of the formula (I). In the formula (II), $R^1$, $R^2$, $R^3$, $R^4$ and $R^5$ each preferably or in particular have those meanings which have already been indicated above, in connection with the description of the compounds of the formula (I) to be prepared according to the invention, as being preferred or particularly preferred for $R^1$, $R^2$, $R^3$, $R^4$ and $R^5$.

The starting materials of the formula (II) are known and/or can be prepared by processes known per se (cf. EP 648749, Preparation Examples).

The formula (IV) provides a general definition of the acrylic acid derivatives further to be used as starting materials in the process (a) according to the invention for preparing compounds of the formula (I) In the formula (IV), $R^7$, $R^8$ and $R^9$ each preferably or in particular have those meanings which have already been indicated above, in connection with the description of the compounds of the formula (I) to be prepared according to the invention, as being preferred or particularly preferred for $R^7$, $R^8$, and $R^9$.

The starting materials of the formula (IV) are known organic chemicals for synthesis.

The formula (III) provides a general definition of the diazonium salts formed as intermediates in the process (a) according to the invention for preparing the compounds of the formula (I). In the formula (III), $R^1$, $R^2$, $R^3$, $R^4$ and $R^5$ each preferably or in particular have those meanings which have already been indicated above, in connection with the description of the compounds of the formula (I) to be prepared according to the invention, as being preferred or particularly preferred for $R^1$, $R^2$, $R^3$, $R^4$ and $R^5$; $X^1$ preferably represents fluorine, chlorine, bromine or iodine, in particular chlorine or bromine.

The compounds of the formula (III) have not yet been disclosed in the literature; as novel substances, they form part of the subject-matter of the present application.

The formula (Ia) provides a general definition of the substituted phenyluracils to be used as starting materials in the process (b) according to the invention for preparing the compounds of the formula (I). In the formula (Ia), $R^1$, $R^2$, $R^3$, $R^4$, $R^5$, $R^7$, $R^8$ and $R^9$ each preferably or in particular have those meanings which have already been indicated above, in connection with the description of the compounds of the formula (I) to be prepared according to the invention, as being preferred or particularly preferred for $R^1$, $R^2$, $R^3$, $R^4$, $R^5$, $R^7$, $R^8$ and $R^9$.

The starting materials of the formula (Ia) are novel compounds according to the invention; they can be prepared by the process (a) according to the invention.

The process (a) according to the invention is carried out using an alkali metal nitrite or alkyl nitrite. These are preferably lithium nitrite, sodium nitrite, potassium nitrite, rubidium nitrite and caesium nitrite, methyl nitrite, ethyl nitrite, n- or i-propyl nitrite, n-, i-, s- or t-butyl nitrite, n-, i-, s- or t-pentyl nitrite, in particular sodium nitrite, potassium nitrite, methyl nitrite, n-, i-, s- or t-butyl nitrite, n-, i-, s- or t-pentyl nitrite.

The process according to the invention is carried out using a hydrogen halide ($HX^1$) or a metal halide ($MX^1$). These are preferably hydrogen fluoride, hydrogen chloride, hydrogen bromide and hydrogen iodide, copper(I) chloride, copper(II) chloride and copper(I) bromide, in particular hydrogen chloride and hydrogen bromide, copper(I) chloride, copper(II) chloride and copper(I) bromide.

The process (a) according to the invention for preparing compounds of the formula (I) is preferably carried out in the presence of a diluent. Suitable diluents are generally the customary organic solvents. These include preferably aliphatic, alicyclic and aromatic, optionally halogenated hydrocarbons such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or carbon tetrachloride, dialkyl ethers such as, for example, diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones such as, for example, acetone, butanone (methyl ethyl ketone), methyl i-propyl ketone or methyl i-butyl ketone, nitriles such as, for example, acetonitrile, propionitrile, butyronitrile or benzonitrile; amides such as, for example, N,N-dimethyl-formamide (DM), N,N-dimethyl-acetamide, N-methyl-formanilide, N-methyl-pyrrolidone or hexamethylphosphoric triamide; esters such as, for example, methyl acetate, ethyl acetate, n- or i-propyl acetate, n-, i- or s-butyl acetate; sulphoxides such as, for example, dimethyl sulphoxide; alkanols such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; (monophasic or multiphasic) mixtures thereof with water or pure water.

When carrying out the process (a) according to the invention, the reaction temperatures can be varied over a relatively wide range. In general, temperatures between −20° C. and +100° C., preferably between −10° C. and +80° C., in particular between 0° C. and 60° C., are employed.

The process (a) according to the invention is generally carried out under atmospheric pressure. However, it is also possible to carry out the process according to the invention under elevated or reduced pressure—in general between 0.1 bar and 10 bar.

In the practice of the process (a) according to the invention, the starting materials are generally employed in approximately equimolar amounts. However, it is also possible to use one of the components in a relatively large excess. The reaction is generally carried out in a suitable diluent and the reaction mixture is generally stirred for several hours at the temperature required. Work-up is carried out according to customary methods (cf. the Preparation Examples).

The process (b) according to the invention for preparing compounds of the formula (I) is preferably carried out in the presence of a suitable acid acceptor. Suitable acid acceptors are generally the customary inorganic or organic bases. These include preferably alkali metal or alkaline earth metal acetates, amides, carbonates, bicarbonates, hydrides, hydroxides or alkoxides such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), and 1,8- diazabicyclo[5,4,0]-undec-7-ene (DBU).

The process (b) according to the invention for preparing compounds of the formula (I) is preferably carried out in the presence of a diluent. Suitable diluents are generally the customary organic solvents. These include preferably aliphatic, alicyclic and aromatic, optionally halogenated hydrocarbons such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or carbon tetrachloride, dialkyl ethers such as, for example, diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones such as, for example, acetone, butanone (methyl ethyl ketone), methyl i-propyl ketone or methyl i-butyl ketone, nitrites such as, for example, acetonitrile, propionitrile, butyronitrile or benzonitrile; amides such as, for example, N,N-dimethyl-formamide (DMF), N,N-dimethyl-acetamide, N-methyl-formanilide, N-methyl-pyrrolidone or hexamethylphosphoric triamide; esters such as, for example, methyl acetate, ethyl acetate, n- or i-propyl acetate, n-, i- or s-butyl acetate; sulphoxides such as, for example, dimethyl sulphoxide; alkanols such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; mixtures thereof with water or pure water.

When carrying out the process (1) according to the invention, the reaction temperatures can be varied over a relatively wide range. In general, temperatures of between −10° C. and 120° C., preferably between 0° C. and 90° C., in particular between 10° C. and 60° C., are employed.

The process (b) according to the invention is generally carried out under atmospheric pressure. However, it is also possible to carry out the process according to the invention under elevated or reduced pressure—in general between 0.1 bar and 10 bar.

In the practice of the process (b) according to the invention, the starting materials are generally employed in approximately equimolar amounts. However, it is also possible to use one of the components in a relatively large excess. The reaction is generally carried out in a suitable diluent in the presence of a reaction auxiliary, and the reaction mixture is generally stirred for several hours at the temperature required. Work-up is carried out according to customary methods (cf. the Preparation Examples).

The active compounds according to the invention can be used as defoliants, desiccants, haulm-killers and, especially, as weed-killers. Weeds, in the broadest sense, are all plants which grow in locations where they are undesired. Whether the compounds according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium. However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of monocotyledonous and dicotyledonous weeds in monocotyledonous and dicotyledonous crops both by the pre- and the post-emergence method.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine encapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as extender, it is also possible to employ for example organic solvents as auxiliary solvents. Essentially, suitable liquid solvents include: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids, can be used in the formulations. Further additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be used as such or, in their formulations, also as a mixture with known herbicides for the control of weeds, in which case ready-to-use formulations or tank mixes are possible.

Suitable co-components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypyr, MCPA, MCPP and triclopyr; aryloxyphenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet, sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and triallate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

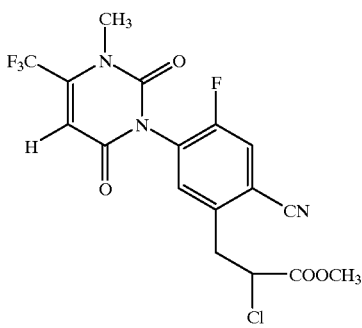

Process (a)

A mixture of 1.8 g (21 mmol) of methyl acrylate, 1.6 g (15.5 mmol) of t-butyl nitrite, 1.6 g (12 mmol) of copper(II) chloride and 50 ml of acetonitrile is cooled to about 0° C., and a solution of 3.3 g (10 mmol) of 1-(5-amino-4-cyano-2-fluorophenyl)-3,6-dihydro-2,6-dioxo-3-methyl-4-trifluoromethyl-1 (2H)-pyrimidine in 20 ml of acetonitrile is added dropwise at this temperature. The reaction mixture is then allowed to warm to room temperature and stirred at this temperature for 18 hours. After the addition of 20 ml of 1N hydrochloric acid, the mixture is then extracted with ethyl acetate and the organic phase is dried with sodium sulphate and filtered. The filtrate is concentrated and the residue is worked-up by column chromatography.

2.8 g (65% of theory) of 1-[4-cyano-2-fluoro-5-(2-chloro-2-methoxycarbonyl-ethyl)-phenyl]-3,6-dihydro-2,6-dioxo-3-methyl-4-trifluoromethyl-1(2H)-pyrimidine of melting point 46° C. are obtained.

Example 2

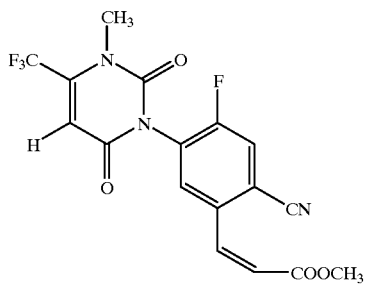

Process (b)

0.22 g of sodium hydride (60%) are added with stirring to a mixture of 2.0 g (4.6 mmol) of 1-[4-cyano-2-fluoro-5-(2-chloro-2-methoxycarbonyl-ethyl)-phenyl]-3,6-dihydro-2,6-dioxo-3-methyltrifluoromethyl-1(2H)-pyrimidine and 30 ml of N,N-dimethyl-formamide which had been cooled to 0° C., and the reaction mixture is initially stirred for 15 minutes at 0° C., then for about 60 minutes at 20° C. and finally for 6 hours at 60° C. The mixture is then concentrated using waterpump vacuum, the residue is stirred with diisopropyl ether and the crystalline product is isolated by filtration with suction.

1.1 g (60% of theory) of 1-[4-cyano-2-fluoro-5-(2-methoxycarbonyl-ethenyl)-phenyl]-3,6-dihydro-2,6-dioxo-3-methyl-4-trifluoromethyl-1(2H)-pyrimidine of melting point 154° C. are obtained.

By the methods of Examples 1 and 2 and according to the general description of the preparation processes according to the invention, it is also possible to prepare, for example, the compounds of the formula (I) listed in Table 1 below.

TABLE 1

Examples of compounds of the formula (I)

(I)

| Ex. No. | R¹ | R² | R³ | R⁴ | R⁵ | R⁶ | Melting point (° C.) |
|---|---|---|---|---|---|---|---|
| 3 | H | CF$_3$ | CH$_3$ | H | CN | —CH$_2$—CH(Cl)—COOCH$_3$ | |
| 4 | H | CF$_3$ | CH$_3$ | F | CSNH$_2$ | —CH$_2$—CH(Cl)—COOCH$_3$ | |
| 5 | H | CF$_3$ | CH$_3$ | F | CN | —CH(CH(CH$_3$)$_2$)—CH(Cl)—... wait |

TABLE 1

Examples of compounds of the formula (I)

| Ex. No. | R¹ | R² | R³ | R⁴ | R⁵ | R⁶ | Melting point (° C.) |
|---|---|---|---|---|---|---|---|
| 3 | H | CF$_3$ | CH$_3$ | H | CN | —CH$_2$—CH(Cl)—COOCH$_3$ | |
| 4 | H | CF$_3$ | CH$_3$ | F | CSNH$_2$ | —CH$_2$—CH(Cl)—COOCH$_3$ | |
| 5 | H | CF$_3$ | CH$_3$ | F | CN | —CH(CH(CH$_3$)$_2$)—CH(Cl)—COOCH$_3$ | |
| 6 | H | CF$_3$ | CH$_3$ | F | CN | —CH(CH(CH$_3$)$_2$)—C(Cl)(CH$_3$)—COOCH$_3$ | |
| 7 | H | CF$_3$ | CH$_3$ | F | CN | —CH(CH$_3$)—CH(Br)—CH(Br)—COOCH$_3$ | |
| 8 | H | CF$_3$ | CH$_3$ | F | CN | —C(CH$_3$)=C(Br)—... —CH=C(Br)—... (CH$_3$)C=CH—COOCH$_3$ with Br | |
| 9 | H | CF$_3$ | CH$_3$ | F | CN | —CH(C$_2$H$_5$)—C(Cl)(CH$_3$)—COOCH$_3$ | |
| 10 | H | CF$_3$ | CH$_3$ | F | CN | —CH=C(CH$_3$)—COOCH$_3$ (with ethyl) | |

TABLE 1-continued

Examples of compounds of the formula (I)

(I)

| Ex. No. | R¹ | R² | R³ | R⁴ | R⁵ | R⁶ | Melting point (° C.) |
|---|---|---|---|---|---|---|---|
| 11 | H | $CF_3$ | $CH_3$ | F | CN | -CH(Cl)-CH$_2$-COOH | |
| 12 | H | $CF_3$ | $CH_3$ | F | CN | -CH=CH-COOH (cis) | |
| 13 | H | $CF_3$ | $CH_3$ | F | CN | -CH=CH-COOC$_2$H$_5$ | 186 |
| 14 | H | $CF_3$ | $CH_3$ | F | CN | -CH=CH-CN | 175 |
| 15 | H | $CF_3$ | $CH_3$ | F | CN | -CH(Cl)-CH$_2$-CN | 85 |
| 16 | H | $CF_3$ | $CH_3$ | F | CN | -CCl$_2$-CH$_2$-CN | |
| 17 | H | $CF_3$ | $CH_3$ | F | CN | -C(Cl)=CH-CN | |
| 18 | H | $CF_3$ | $CH_3$ | F | $CSNH_2$ | -CH=CH-COOC$_2$H$_5$ | |
| 19 | H | $CF_3$ | $CH_3$ | F | $CSNH_2$ | -CH(Cl)-CH$_2$-COOH | |

TABLE 1-continued

Examples of compounds of the formula (I)

(I)

| Ex. No. | R¹ | R² | R³ | R⁴ | R⁵ | R⁶ | Melting point (° C.) |
|---|---|---|---|---|---|---|---|
| 20 | $CH_3$ | $CF_3$ | $CH_3$ | F | CN | -CH(Cl)-CH(CH$_2$CH$_3$)-COOH | |
| 21 | H | $CF_3$ | $CH_3$ | F | CN | -CH(Cl)-CH(CH$_2$CH$_3$)-COOC$_2$H$_5$ | |
| 22 | H | $CF_3$ | $CH_3$ | F | CN | -C(Cl)(CH$_3$)-C(CH$_2$CH$_3$)-COOC$_2$H$_5$ | |
| 23 | H | $CF_3$ | $CH_3$ | F | CN | -CH(Cl)-CH(CH$_2$CH$_3$)-CO-O-CH$_3$ | 173 |
| 24 | H | $CF_3$ | $CH_3$ | F | CN | -C(Cl)(CH$_3$)-C(CH$_2$CH$_3$)-CO-H | 159 |
| 25 | H | $CF_3$ | $CH_3$ | F | CN | -CH=CH(CH$_2$CH$_3$)-CO-CH$_3$ | 186 |
| 26 | H | $CF_3$ | $CH_3$ | F | CN | -C(CH$_3$)=C(CH$_2$CH$_3$)-COOC$_2$H$_5$ | |
| 27 | H | $CF_3$ | $CH_3$ | F | CN | -C(CH$_3$)=C(CH$_2$CH$_3$)-CO-O-CH$_3$ | 197 |

STARTING MATERIALS OF THE FORMULA (II)

Example (II-1)

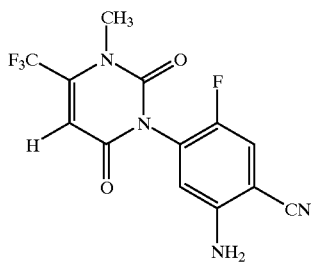

0.17 g (1.2 mmol) of pivaloyl chloride is added with stirring to a mixture of 0.50 g (1.2 mmol) of 1-(4-cyano-2-fluoro-5-trifluoroacetylamino-phenyl)-3,6-dihydro-2,6-dioxo-3-methyl-4-trifluoromethyl-1(2H)-pyrimidine, 1 ml of triethylamine and 50 ml of acetonitrile, and the reaction mixture is stirred for 18 hours at 20° C. and for a further 15 hours at 60° C. The mixture is then concentrated using waterpump vacuum, the residue is shaken with 1N hydrochloric acid/ethyl acetate and the organic phase is separated off, dried with sodium sulphate and filtered. The filtrate is concentrated using waterpump vacuum and the residue is worked-up by column chromatography (silica gel, chloroform/ethyl acetate, 1:1 (v:v)).

In addition to unreacted 1-(4-cyano-2-fluoro-5-trifluoroacetylamino-phenyl)-3,6-dihydro-2,6-dioxo-3-methyl-4-trifluoromethyl-1(2H)-pyrimidine (first fraction: 0.30 g), 0.2 g (50% of theory) of 1-(4-cyano-2-fluoro-5-amino-phenyl)-3,6-dihydro-2,6-dioxo-3-methyl-4-trifluoromethyl-1(2H)-pyrimidine is obtained as second fraction. Melting point: 195° C.

USE EXAMPLES

Example A

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered with the preparation of the active compound. It is advantageous to keep the amount of water per unit area constant. The concentration of the active compound in the preparation is immaterial, only the amount of active compound applied per unit area matters.

After three weeks, the degree of damage to the plants is rated in % damage by comparison with the development of the untreated control.

The figures denote:

0%=no effect (like untreated control)

100%/=total destruction

In this test, strong activity against weeds was shown by the compounds of the formula (I).

Example B

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular desired amounts of active compound are applied in about 1000 l/ha.

After three weeks, the degree of damage to the plants is rated in % damage by comparison with the development of the untreated control.

The figures denote:

0%=no effect (like untreated control)

100%=total destruction

In this test, strong activity against weeds such as Abutilon (100%), Amaranthus (100%), Galium (100%), Xanthium (100%), Setaria (100%) and Avena fatua (95%) is shown by the compounds of Preparation Examples 1 and 2 at application rates of 125 g/ha.

What is claimed is:

1. A compound of formula (I)

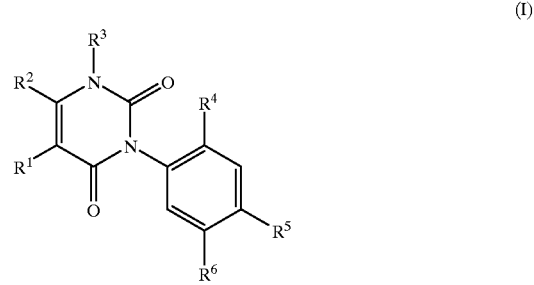

wherein $R^1$ represents hydrogen, fluorine, chlorine, bromine or optionally fluorine- and/or chlorine-substituted $C_1$–$C_4$-alkyl, $R^2$ represents optionally fluorine- and/or chlorine-substituted $C_1$–$C_4$-alkyl, $R^3$ represents hydrogen, amino, optionally cyano-, chlorine- or $C_1$–$C_4$-alkoxy-substituted $C_1$–$C_6$-alkyl or optionally fluorine- and/or chlorine-substituted $C_2$–$C_6$-alkenyl or $C_2$–$C_6$-alkinyl, $R^4$ represents hydrogen, cyano, fluorine or chlorine, $R^5$ represents cyano or thiocarbamoyl, and $R^6$ represents one of the groupings below $C(R^7, R^8)$—$C(R^7, R^8)$—$R^9$ or —$C(R^7)$=$C(R^8)$—$R^9$ in which $R^7$ and $R^8$ are identical or different and each represents independently of the other hydrogen, hydroxyl, mercapto, fluorine, chlorine, bromine or respectively optionally cyano-, fluorine-, chlorine- or $C_1$–$C_4$- alkoxy-substituted $C_1$–$C_4$-alkyl, $C_1$–$C_4$-alkoxy or $C_1$–$C_4$- alkylthio, and $R^9$ represents cyano, formyl, $C_1$–$C_4$-alkylcarbonyl, the grouping —CO—OR$^{10}$ or the grouping —CO—N($R^{11}$, $R^{12}$), where $R^{10}$ represents hydrogen or represents optionally cyano-, fluorine-, chlorine- or $C_1$–$C_4$-alkoxy-substituted $C_1$–$C_{10}$-alkyl, $R^{10}$ furthermore represents respectively optionally fluorine-, chlorine- or bromine-substituted $C_3$–$C_{10}$-alkenyl or $C_3$–$C_{10}$-alkinyl, $R^{10}$ furthermore represents respectively optionally cyano-, fluorine-, chlorine-, bromine-, $C_1$–$C_4$-alkyl- or $C_1$–$C_4$-alkoxy-carbonyl-substituted $C_3$–$C_6$-cycloalkyl or $C_3$–$C_6$-cycloalkyl-$C_1$–$C_4$-alkyl, $R^{10}$ furthermore represents respectively optionally cyano-, fluorine, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio, $C_1$–$C_4$-halogenoalkylthio- or $C_1$–$C_4$-alkoxy-carbonyl-substituted phenyl, phenyl-$C_1$–$C_4$-alkyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxazolylmethyl, thiazolyl, thiazolylmethyl, oxadiazolyl, oxadiazolylmethyl, thiadiazolyl, thiadiazolylmethyl, dioxolanyl, dioxolanyl methyl, pyridinyl, pyridinylmethyl, pyrimidinyl or pyrimidinylmethyl, $R^{11}$ represents hydrogen or represents respectively optionally cyano-, fluorine-, chlorine- or $C_1$–$C_4$-alkoxy-substituted $C_1$–$C_6$-alkyl or $C_1$–$C_6$-alkoxy, $R^{11}$ furthermore represents respectively optionally fluorine-, chlorine- or bromine-substituted $C_3$–$C_6$-alkenyl or $C_3$–$C_6$-alkinyl, and $R^{12}$ represents hydrogen or represents optionally cyano-, fluorine-, chlorine- or $C_1$–$C_4$-alkoxy-substituted $C_1$–$C_{10}$-alkyl, $R^{12}$ furthermore represents respectively optionally fluorine-, chlorine- or bromide-substituted $C_3$–$C_{10}$-alkenyl or $C_3$–$C_{10}$-alkinyl, $R^{12}$ furthermore represents respectively optionally cyano-, fluorine-, chlorine-, bromine-, $C_1$–$C_4$-alkyl- or $C_1$–$C_4$-alkoxy-carbonyl-substituted $C_3$–$C_6$-cycloalkyl or $C_3$–$C_6$-cycloalkyl-$C_1$–$C_4$-alkyl, $R^{12}$ furthermore represents respectively optionally cyano-, fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio- or $C_1$–$C_4$-alkoxy-carbonyl-substituted phenyl, phenyl-$C_1$–$C_4$-alkyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl or together with $R^{11}$ represents $C_2$–$C_6$-alkanediyl.

2. The compound according to claim 1 wherein $R^1$ represents hydrogen, fluorine, chlorine, bromine or optionally fluorine and/or chlorine-substituted methyl or ethyl, $R^2$ represents optionally fluorine- and/or chlorine-substituted methyl or ethyl, $R^3$ represents hydrogen, amino, represents optionally cyano-, fluorine-, chlorine-, methoxy- or ethoxy-substituted methyl, ethyl, n- or i-propyl, n-, i-, - or t-butyl, or represents optionally fluorine- and/or chlorine-substituted propenyl, butenyl, propinyl or butinyl, $R^4$ represents hydrogen, fluorine or chlorine, $R^5$ represents cyano or thiocarbamoyl, and $R^6$ represents one of the groupings below —C($R^7$,$R^8$)—C($R^7$,$R^8$)—$R^9$ or —C($R^7$)=C($R^8$)—$R^9$ in which $R^7$ and $R^8$ are identical or different and each represents independently of the other hydrogen, fluorine, chlorine, bromine or respectively optionally cyano-, fluorine-, chlorine-, methoxy- or ethoxy-substituted methyl, ethyl, methoxy, ethoxy, methylthio or ethylthio, and $R^9$ represents cyano, the grouping —CO—OR$^{10}$ or the grouping —CO—N($R^{11}$,$R^{12}$), where $R^{10}$ represents hydrogen or represents optionally cyano-, fluorine-, chlorine-, methoxy- or ethoxy-substituted methyl, ethyl, n- or i-propyl, n-, i-, s- or t-butyl, n-, i-, s- or t-pentyl, $R^{10}$ furthermore represents respectively optionally fluorine-, chlorine- or bromine-substituted propenyl, butenyl, pentenyl, propinyl, butinyl or pentinyl, $R^{10}$ furthermore represents respectively optionally cyano-, fluorine-, chlorine-, bromine-, methyl-, ethyl-, methoxycarbonyl- or ethoxycarbonyl-substituted cyclopropyl, cyclobutyl, cyclopentyl, cyclohexyl, cyclopropylmethyl, cyclobutylmethyl, cyclopentylmethyl or cyclohexylmethyl, $R^{10}$ furthermore represents respectively optionally cyano-, fluorine-, chlorine-, bromine-, methyl-, ethyl-, trifluoromethyl-, methoxy-, ethoxy-, difluoromethoxy-, trifluoromethoxy-, methylthio-, ethylthio-, difluoromethylthio-, trifluoromethyl-, methoxycarbonyl- or ethoxycarbonyl-substituted phenyl, phenylmethyl, phenylethyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl, $R^{11}$ represents hydrogen or represents respectively optionally cyano-, fluorine-, chlorine-, methoxy- or ethoxy-substituted methyl, ethyl, methoxy or ethoxy, $R^{11}$ furthermore represents respectively optionally fluorine-, chlorine- or bromine-substituted propenyl or propinyl, and $R^{12}$ represents hydrogen or represents optionally cyano-, fluorine-, chlorine-, methoxy- or ethoxy-substituted methyl, ethyl, n- or i-propyl, n-, i-, s- or t-butyl, n-, i-, s- or t-pentyl, $R^{12}$ furthermore represents respectively optionally fluorine-, chlorine- or bromine-substituted propenyl butenyl, pentenyl, propinyl, butinyl or pentinyl, respectively optionally cyano-, fluorine-, chlorine-, bromine-, methyl-, ethyl-, methoxycarbonyl- or ethoxy-carbonyl-substituted cyclopropyl, cyclobutyl, cyclopentyl, cyclohexyl, cyclopropylmethyl, cyclo-butylmethyl, cyclopentylmethyl or cyclohexylmethyl, $R^{12}$ furthermore represents respectively optionally cyano-, fluorine-, chlorine-, bromine-, methyl-, ethyl-, trifluoromethyl-, methoxy-, ethoxy-, difluoromethoxy-, trifluoromethoxy-, methylthio-, ethylthio-, difluoromethylthio-, trifluoromethylthio-, methoxycarbonyl- or ethoxycarbonyl-substituted phenyl, phenylmethyl, phenylethyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxazolylmethyl thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl.

3. An herbicidal composition comprising an herbicidally effective amount of a compound according to claim 1 and an extender or surfactant.

4. A method of controlling unwanted vegetation which comprises applying to such vegetation or to a locus from which it is desired to exclude such vegetation an herbicidally effective amount of a compound according to claim 1.

5. A compound of the formula (III):

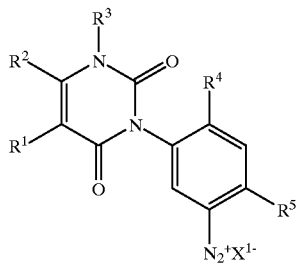

(III)

wherein $R^1$ represents hydrogen, fluorine, chlorine, bromine or optionally fluorine- and/or chlorine-substituted $C_1$–$C_4$-alkyl, $R^2$ represents optionally fluorine- and/or chlorine-substituted $C_1$–$C_4$-alkyl, $R^3$ represents hydrogen, amino, optionally cyano-, fluorine-, chlorine- or $C_1$–$C_4$-alkoxy-substituted $C_1$–$C_6$-alkyl or optionally fluorine- and/or chlorine-substituted $C_2$–$C_6$-alkenyl or $C_2$–$C_6$-alkinyl, $R^4$ represents hydrogen cyano, fluorine or chlorine, $R^5$ represents cyano or thiocarbamoyl, and $X^1$ represents halogen.

6. A compound of the formula (Ia):

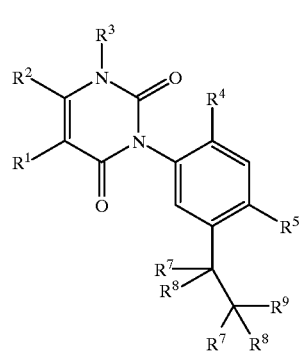

(Ia)

wherein $R^1$ represents hydrogen, fluorine, chlorine, bromine or optionally fluorine- and/or chlorine-substituted $C_1$–$C_4$-alkyl, $R^2$ represents optionally fluorine- and/or chlorine-substituted $C_1$–$C_4$-alkyl, $R^3$ represents hydrogen, amino, optionally cyano-, fluorine-, chlorine- or $C_1$–$C_4$-alkoxy-substituted $C_1$–$C_6$-alkyl or optionally fluorine- and/or chlorine-substituted $C_2$–$C_6$-alkenyl or $C_1$–$C_6$-alkinyl, $R^4$ represents hydrogen, cyano, fluorine or chlorine, $R^5$ represents cyano or thiocarbamoyl, and $R^6$ represents one of the groupings below

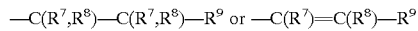
—C($R^7$,$R^8$)—C($R^7$,$R^8$)—$R^9$ or —C($R^7$)=C($R^8$)—$R^9$ in which $R^7$ and $R^8$ are identical or different and each represents independently of the other hydrogen, hydroxyl, mercapto, fluorine, chlorine, bromine or respectively optionally cyano-, fluorine-, chlorine- or $C_1$–$C_4$-alkoxy-substituted $C_1$–$C_4$-alkyl, $C_1$–$C_4$-alkoxy or $C_1$–$C_4$-alkylthio, and $R^9$ represents cyano, formyl, $C_1$–$C_4$-alkyl-carbonyl, the grouping —CO—$OR^{10}$ or the grouping —CO—N($R^{11}$, $R^{12}$), where $R^{10}$ represents hydrogen or represents optionally cyano-, fluorine-, chlorine- or $C_1$–$C_4$-alkoxy-substituted $C_1$–$C_{10}$-alkyl, $R^{10}$ furthermore represents respectively optionally fluorine-, chlorine- or bromine-substituted $C_3$–$C_{10}$-alkenyl or $C_3$–$C_{10}$-alkinyl, $R^{10}$ furthermore represents respectively optionally cyano-, fluorine-, chlorine-, bromine-, $C_1$–$C_4$-alkyl- or $C_1$–$C_4$-alkoxy-carbonyl-substituted $C_3$–$C_6$-cycloalkyl or $C_3$–$C_6$-cycloalkyl-$C_1$–$C_4$-alkyl, $R^{10}$ furthermore represents respectively optionally cyano-, fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio- or $C_1$–$C_4$-alkoxy-carbonyl-substituted phenyl, phenyl-$C_1$–$C_4$-alkyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxadiazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl, $R^{11}$ represents hydrogen or represents respectively optionally cyano-, fluorine-, chlorine- or $C_1$–$C_4$-alkoxy-substituted $C_1$–$C_6$-alkyl or $C_1$–$C_6$-alkoxy, $R^{11}$ furthermore represents respectively optionally fluorine-, chlorine- or bromine-substituted $C_3$–$C_6$-alkenyl or $C_3$–$C_6$-alkinyl, and $R^{12}$ represents hydrogen or represents optionally cyano-, fluorine-, chlorine- or $C_1$–$C_4$-alkoxy-substituted $C_1$–$C_{10}$-alkyl, $R^{12}$ furthermore represents respectively optionally fluorine-, chlorine- or bromine-substituted $C_3$–$C_{10}$-alkenyl or $C_3$–$C_{10}$-alkinyl, $R^{12}$ furthermore represents respectively optionally cyano-, fluorine-, chlorine-, bromine-, $C_1$–$C_4$-alkyl- or $C_1$–$C_4$-alkoxy-carbonyl-substituted $C_3$–$C_6$-cycloalkyl or $C_3$–$C_6$-cycloalkyl-$C_1$–$C_4$-alkyl, $R^{12}$ furthermore represents respectively optionally cyano-, fluorine-, chlorine-, bromine-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio- or $C_1$–$C_4$-alkoxy-carbonyl-substituted phenyl, phenyl-$C_1$–$C_4$-alkyl, furyl, furylmethyl, tetrahydrofuryl, tetrahydrofurylmethyl, thienyl, thienylmethyl, tetrahydrothienyl, tetrahydrothienylmethyl, perhydropyranyl, perhydropyranylmethyl, oxazolyl, oxadiazolylmethyl, thiazolyl, thiazolylmethyl, oxadiazolyl, oxadiazolylmethyl, thiadiazolyl, thiadiazolylmethyl, dioxolanyl, dioxolanylmethyl, pyridinyl, pyridinylmethyl, pyrimidinyl or pyrimidinylmethyl or together with $R^{11}$ represents $C_2$–$C_6$-alkanediyl.

\* \* \* \* \*